United States Patent [19]

Kawamonzen

[11] Patent Number: 5,569,763

[45] Date of Patent: Oct. 29, 1996

[54] HYDRAZONE COMPOUND AND THE USE THEREOF

[75] Inventor: Yoshiaki Kawamonzen, Kawasaki, Japan

[73] Assignee: Kabushiki Kaisha Toshiba, Kawasaki, Japan

[21] Appl. No.: 401,684

[22] Filed: Mar. 10, 1995

[30] Foreign Application Priority Data

Mar. 15, 1994 [JP] Japan ................................ 6-042980
Sep. 27, 1994 [JP] Japan ................................ 6-230840

[51] Int. Cl.⁶ ........................ C07D 401/02; C07D 401/14
[52] U.S. Cl. ........................ 546/256; 544/237; 544/238; 544/284; 544/333; 544/353; 544/405; 546/106; 546/145; 546/176; 546/264; 546/269.7; 546/270.1; 546/273.4; 546/272.7; 546/275.4
[58] Field of Search ........................ 544/237, 284, 544/353, 238, 333, 405; 546/106, 145, 176, 264, 278, 280, 281, 283, 284, 156; 514/248, 249, 259, 252, 256, 298, 307, 314, 332, 336, 341, 342, 343

[56] References Cited

FOREIGN PATENT DOCUMENTS 0430385 6/1991 European Pat. Off. .
9213846 8/1992 WIPO .

OTHER PUBLICATIONS

Owen, J. R., et al.; Journal of Materials Science, 11(Letters), 2165–2169; "Second Harmonic Geneystals"; 1976.
Ishii, Hajime, et al. "Synthesis of Sensitive Pyridylhydrazone Reagents and Extraction–Spectrophotometric Determination of Trace Nickel with 2–Pyridinecarbaldehyde 2–(5–Nitro)pyridylhydrazone"; Analytical Sciences, Aug. 1987, vol. 3, pp. 347–352.

Prescott et al, J. of Pharm. Sciences, vol. 59, No. 1, Jan. 1970, pp. 101–104.

*Primary Examiner*—Zinna Northington Davis
*Attorney, Agent, or Firm*—Oblon, Spivak, McClelland, Maier & Neustadt, P.C.

[57] ABSTRACT

Hydrazone compound useful as an excellent organic nonlinear optical material and a highly sensitive coloring chelation agent, represented by the following formula (1):

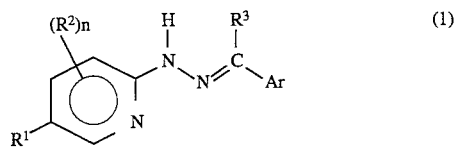

wherein

Ar is a substituted or an non-substituted 2-imidazolyl group, a 4-imidazolyl group, 3-pyrazolyl group, 3-pyridazinyl, 2-pyrimidinyl, 4-pyrimidinyl, 2-quinolyl, 1-isoquinolyl, 3-isoquinolyl, 1-phthalazinyl, 2-quinazolinyl, 2-benzimidazolyl, 2-benzothiazolyl, or 2-thiazolyl group, $R^1$ is a nitro group, cyano group or trifluoromethyl group, $R^2$ is a nitro group, cyano group, trifluoromethyl group or a halogen atom, or a substituted or an non-substituted alkyl group, $R^3$ is a hydrogen atom, and n is an integer from 0 to 3.

6 Claims, 1 Drawing Sheet

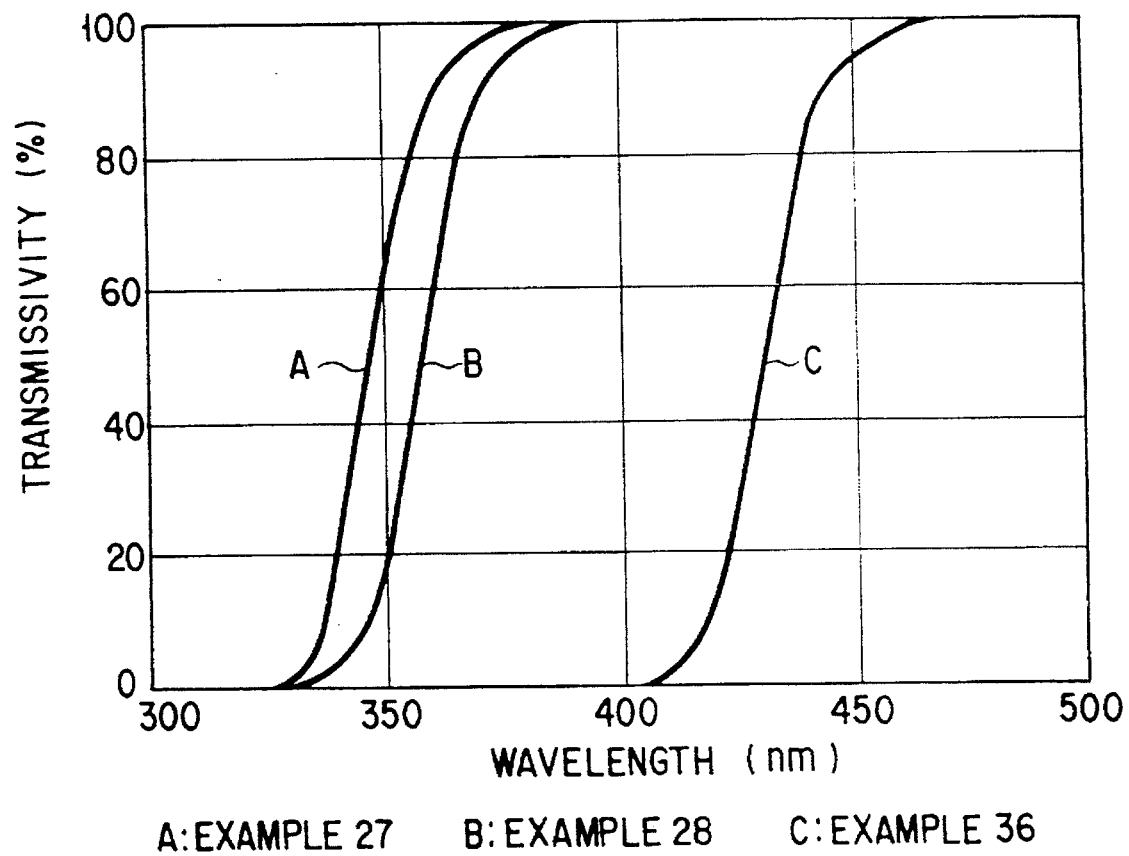
FIGURE

HYDRAZONE COMPOUND AND THE USE THEREOF

BACKGROUND OF THE INVENTION

1. Field of the Invention

The present invention relates to a novel hydrazone compound and the use thereof in a nonlinear optical material and as an organic chelating agent.

2. Description of the Related Art

A nonlinear optical effect is applied to modulate the wavelength, phase and amplitude of a laser light in case of harmonics generation, optical switching, and optical mixing. The effect thus plays an important role in the field of information processing using light.

Hitherto, inorganic compound crystals have been mostly used as a nonlinear optical material exhibiting a nonlinear optical effect. However, their nonlinear optical effects are unsatisfactory. Recently, besides the inorganic compound crystals, various organic compounds have been found to possess a nonlinear optical constant considerably larger than those of inorganic compound crystals and to exhibit excellent resistance to optical damage.

General information on the organic nonlinear optical materials is disclosed in, for example, D. J. Williams et al., "Nonlinear Optical Properties of Organic and Polymeric Materials", American Chemical Society, 1983, and D.S. Chemla et al., "Nonlinear Optical Properties of Organic Molecules and Crystals", Academic Press Inc, 1987. The organic nonlinear optical material listed in these publications has a structural feature at a molecular level that an electron-donating functional group is allowed to bind to one end of a π electron-system skeleton such as a benzene ring, and an electron-attractive functional group is allowed to bind to the other end thereof.

However, in the ground state, a molecule having the aforementioned structure has electric dipoles which tend to oppose each other to assume an energetically stable condition. Accordingly, when crystallized, the aforementioned molecule comes to have a structure with a symmetrical center. Because of the symmetrical structure, the large nonlinearity of each molecule can be canceled out at an entire crystal level. This feature of the crystallized structure has posed a problem that the excellent nonlinear optical effect expected on the basis of its molecular structure cannot be obtained at the entire crystal level.

For the reasons mentioned above, there has been a considerable demand for an organic nonlinear optical material having excellent nonlinearity not only at a molecular level, but also at the entire crystal level.

On the other hand, in the field of organic coloring agents, a wide variety of organic chelating agents have been used heretofore. In this field, Nilson reported oxalic bis(cyclohexylidene hydrazide) whose conventional name is cuprizone in 1950 [G. Nilson, Acta Chemica Scandinavia, 4,205 (1950)]. Since then, hydrazone compounds have been drawn attention as organic coloring agents for various metal ions. Characteristics which are required for the organic coloring agents include specificity, selectivity, sensitivity and the like. Since cuprizone is well-balanced in terms of such characteristics, it is widely used at present as a coloring agent for various metal ions. However, since the requirement for micro chemical analysis has increased over time, particularly, in absorption spectrophotometry, the development of an organic coloring agent more sensitive than the existing one is greatly demanded.

SUMMARY OF THE INVENTION

A first object of the present invention is to provide a hydrazone compound useful as an organic nonlinear optical material having excellent nonlinearity and generating harmonics efficiently, as well as being useful as a highly-sensitive coloring chelating agent.

A second object of the present invention is to provide an organic nonlinear optical material exhibiting excellent nonlinearity and generating harmonics efficiently and to provide a method for obtaining nonlinear optical effect using this organic nonlinear optical material.

A third object of the present invention is to provide a highly sensitive coloring chelation agent and a method for analyzing a metal ion in a solution using this agent.

The aforementioned objects can be attained by a hydrazone compound represented by the following formula (1):

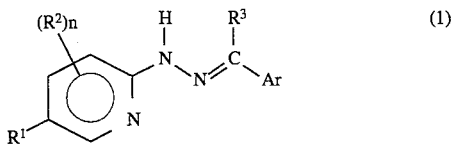

wherein Ar, $R^1$ to $R^3$, and n, each denotes the groups described below, with the exception of the case where Ar is a 2-pyridyl group, $R^1$ is a nitro group, $R^3$ is hydrogen and n is zero.

Ar: 2-pyridyl, 2-imidazolyl, 4-imidazolyl, 3-pyrazolyl, 2-thiazolyl, 2-pyrrolyl, 3-indolyl, 2-furyl, 2-thienyl, phenyl, 3-pyridyl, 4-pyridyl, 3-pyridazinyl, 2-pyrimidinyl, 4-pyrimidinyl, 2-pyrazinyl, 3-cinnolinyl, 1-phthalazinyl, 2-quinazolinyl, 4-quinazolinyl, 2-quinoxalinyl, 2-benzothiazolyl, 2-benzimidazolyl, 2-quinolyl, 1-isoquinolyl, 3-isoquinolyl, or 6-phenanthridinyl. All these groups may be either substituted or non-substituted.

$R^1$: nitro, cyano, or trifluoromethyl, $R^2$: nitro, cyano, trifluoromethyl, a halogen, or a substituted or non-substituted alkyl.

$R^3$: alkyl, aryl, 2-pyridyl, 2-imidazolyl, 4-imidazolyl, 3-pyrazolyl, 2-thiazolyl, 2-pyrrolyl, 3-indolyl, 2-furyl, 2-thienyl, 3-pyridyl, 4-pyridyl, 3-pyridazinyl, 2-pyrimidinyl, 4-pyrimidinyl, 2-pyrazinyl, 3-cinnolinyl, 1-phthalazinyl, 2-quinazolinyl, 4-quinazolinyl, 2-quinoxalinyl, 2-benzothiazolyl, 2-benzimidazolyl, 2-quinolyl, 1-isoquinolyl, 3-isoquinolyl, 6-phenanthridinyl or hydrogen atom. These groups except for a hydrogen atom may be either substituted or non-substituted.

n: an integer from 0 to 3

The hydrazone compound of the present invention can be easily synthesized in an organic solvent such as ethanol through the dehydration-condensation of 2-pyridylhydrazine compound with a heteroaryl aldehyde compound, a heteroaryl ketone compound or a heteroaryl azomethine compound, in the presence of an acid catalyst such as acetic acid or hydrochloric acid.

The second object of the present invention can be attained by the organic nonlinear optical material comprising a crystal of the hydrazone compound represented by the formula (1) or attained by a method of obtaining a nonlinear optical effect by irradiating an organic nonlinear optical material with light, in which the organic nonlinear optical material comprising of a hydrazone compound represented by the formula (1).

The third object of the present invention can be attained by an organic chelating agent comprising a hydrazone compound represented by the formula (1) or attained by a method of analyzing a metal ion contained in a solution, comprising the steps of:

forming a metal complex selectively between an organic chelating agent and a metal ion by adding the organic chelating agent in the solution; and detecting color intrinsic to the metal complex, in which a hydrazone compound is used as the chelating agent.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

Attached Figure is a visible-ultraviolet transmission spectra of hydrazone compounds of Examples 27, 28 and 36, measured in 0.001M ethanol solution.

DETAILED DESCRIPTION OF THE PREFERRED EMBODIMENTS

The hydrazone compound of the present invention represented by the formula (1) has the following general characteristics as an organic nonlinear optical material.

In the formula (1), the amino group (—NH—) bound to a pyridine ring acts as an electron-donating group. On the other hand, $R^1$, namely a nitro group (—NO$_2$), a cyano group (—CN) or a trifluoromethyl group (—CF$_3$) acts as an electron-attractive group. That is, in the hydrazone compound (1), the electron-donating functional group binds to one end of a π electron system skeleton and the electron-attractive functional group binds to the other end thereof. Consequently, molecular polarization due to a resonance effect (mesomeric polarization) increases, so that the hydrazone compound acquires high degree of nonlinearity at a molecular level.

Furthermore, in the molecules of the hydrazone compound (1), molecular orientation at the time of crystallization, is controlled by intermolecular hydrogen bonds. These hydrogen bonds are formed in such a way that electric dipoles of individual molecules are lined in the same direction, as shown in the following illustration.

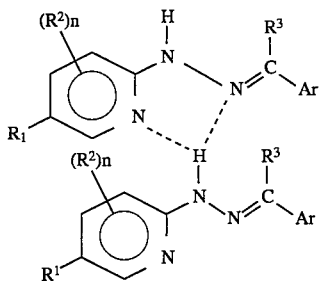

More specifically, the intermolecular hydrogen bonds allow individual molecules to orient in such a way that individual dipolar moments are amplified by duplicating to each other. By virtue of this function of the hydrogen bonds, each molecule can resist to reverse-intermolecular orientation force caused by electrical interaction between dipoles. Accordingly, the molecule of the hydrazone compound (1) tends to form a crystal structure which has no asymmetric center and thus it has excellent nonlinear optical properties even in the crystal state.

A particularly preferable example in this respect is a hydrazone compound in which Ar of the formula (1) is a nitrogen-containing heterocyclic aromatic group having a pyridine-type nuclear nitrogen atom (—N═), such as a 2-pyridyl, 2-imidazolyl, 4-imidazolyl, 3-pyrazolyl, 3-pyridazinyl, 2-pyrimidinyl, 4-pyrimidinyl, 2-quinolyl, 1-isoquinolyl, 3-isoquinolyl, 1-phthalazinyl, 2-quinazolinyl, 2-benzimidazolyl, 2-benzothiazolyl, or 2-thiazolyl; wherein Ar binds to a hydrazone carbon via a nuclear carbon atom at the α-position of the nuclear nitrogen atom. In such an example, the orientation of the molecules can be also controlled by second intermolecular hydrogen bonds in addition to the aforementioned intermolecular hydrogen bonds, in such a way that dipolar moments are lined in the same direction, as shown in the following illustration.

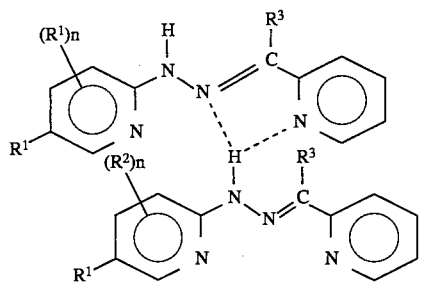

More specifically, in this case, a stable intramolecular hydrogen bond is generated between a hydrogen atom of an amino group (—NH—) in a hydrazone skeleton, a nitrogen atom of an azomethine group (—N═CH—) and a pyridine-type nuclear nitrogen atom (—N═) of nitrogen-containing heterocyclic aromatic group Ar. By virtue of the stable intramolecular hydrogen bond, a crystal structure having no asymmetric center can be easily formed. Accordingly, in an example of such a hydrazone compound having the second intramolecular hydrogen bonds mentioned above, the nonlinear optical effect in a crystal state can be further improved.

The hydrazone compound of the present invention also has a high melting point and excellent heat resistance by virtue of the aforementioned stable intramolecular hydrogen bonds. Hence, the hydrazone compound of the present invention can overcome a heat-resistance problem which is considered a drawback in conventional organic nonlinear optical materials. A preferable example in this respect is a hydrazone compound represented by the following formula (2) or (3):

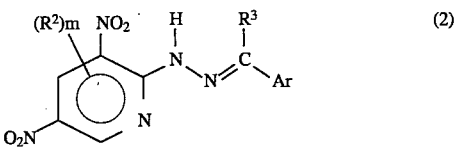

(2)

wherein Ar, $R^1$ to $R^3$ and n are as defined above; and m is an integer from 0 to 2.

Compound (2) differs from compound (1) in that $R^1$ is restricted to a nitro group and at least one of $R^2$ is restricted to a nitro group at the β position in respect to $R^1$.

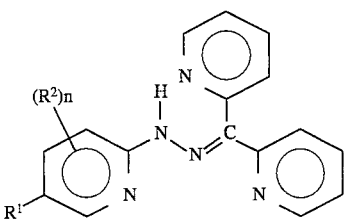

(3)

Compound (3) differs from compound (1) in that both Ar and $R^3$ are restricted to 2-pyridyl group. In this compound, in addition to the intermolecular hydrogen bonds mentioned above, an intramolecular hydrogen bond shown by a broken line is formed between a hydrogen atom of an amino group (—NH—) in a hydrazone skeleton and a nuclear nitrogen atom (—N=) of a pyridine ring which is not associated with the intermolecular hydrogen bonds. The intermolecular hydrogen bond thus formed also contributes to raising a melting point of a crystal and thus the heat resistance of an organic nonlinear optical material is further remarkably improved. The reason why the intramolecular hydrogen bond contributes to raising the melting point is presumably that much denser crystalline structure is obtained from a flat configuration of the entire molecule which is resulted from the fact that the intramolecular hydrogen bond control the configuration of the pyridine ring so as to be in a flat form, as shown above.

A preferable example in another respect is a hydrazone compound in which an electron attractive group $R^1$ of the formula (1) is a cyano group or a trifluoromethyl group. In the compound of this example, an optical absorption band remarkably shifts to a short-wavelength zone outside of a visible light region due to the electron attractive group, resulting in no optical absorption being present in the visible-light range which is important for a nonlinear optical element. Hence, light transmissivity in a blue color wavelength range is enhanced and harmonics in the range can be efficiently generated and utilized.

Furthermore, the hydrazone compound of the present invention has an excellent feature as a highly sensitive coloring chelation agent. More specifically, the compound of the present invention represented by the formula (1) forms a metal complex having a large molar absorptivity by coordinated to nickel (II), cobalt (II), copper (II), zinc (II), iron (II), palladium (II) in an aqueous solution (or a mixed solution of an organic solvent and water) in the pH range from acidic to poor alkaline. In addition, the hydrazone compound has excellent selectivity for metals in the complex formation reaction. Hence, the hydrazone compound of the present invention can be used as a highly-sensitive coloring chelation agent for quantitative microanalysis of metal ions using absorption spectrophotometry.

Hereinbelow, the present invention will be described in detail by way of Examples, however the present invention will not limited by the Examples.

(A) Examples of hydrazone compound synthesis

EXAMPLE 1

Synthesis of 2-imidazolecarbaldehyde-(5-nitro-2-pyridyl)hydrazone (compound 1)

3.10 g (20.1 mmol) of 5-nitro-2-pyridylhydrazine and 2.00 g (20.8 mmol) of 2-imidazolecarbaldehyde were dissolved in 50 ml of ethanol. To this mixture, 1 ml of acetic acid was added and heated under reflux for 2 hours while being stirred. After the resultant reaction mixture was allowed to stand still overnight, coarse crystals precipitated were filtrated by the suction-filtration. The obtained coarse crystals were recrystallized from a hot ethanol solution to obtain a desired product.

Yield: 3.28 g (14.1 mmol) [yield rate: 70%]

Melting point: 268° to 269° C.

C-N stretching vibration (IR spectrum) of an azomethine group (—N=CH—): 1600 $cm^{-1}$ (measured by KBr method)

δ value ($^1$H-NMR spectrum) of a hydrogen atom of an azomethine group (—N=CH—): 7.96 ppm (solvent: tetrahydrofuran-$d_8$)

Element analysis: molecular formula: $C_9H_8N_6O_2$ molecular weight: 232.203

|  | Carbon | Hydrogen | Nitrogen |
| --- | --- | --- | --- |
| Calculation value | 46.6% | 3.5% | 36.2% |
| Analysis value | 46.4% | 3.5% | 36.3% |

EXAMPLE 2

Synthesis of 4-imidazolecarbaldehyde-(5-nitro-2-pyridyl)hydrazone (compound 2)

A desired product was obtained in the same manner as in Example 1 by using 3.10.g (20.1 mmol) of 5-nitro-2-pyridylhydrazine and 2.00 g (20.8 mmol) of 4-imidazolecarbaldehyde.

Yield: 3.50 g (15.1 mmol) [yield rate: 75%]

Melting point: 297° to 298° C.

C-N stretching vibration (IR spectrum) of an azomethine group (—N=CH—): 1595 $cm^{-1}$ (measured by KBr method)

δ value ($^1$H-NMR spectrum) of a hydrogen atom of an azomethine group (—N=CH—): 7.86 ppm (solvent: tetrahydrofuran-$d_8$)

Element analysis: molecular formula: $C_9H_8N_6O_2$ molecular weight: 232.203

|  | Carbon | Hydrogen | Nitrogen |
| --- | --- | --- | --- |
| Calculation value | 46.6% | 3.5% | 36.2% |
| Analysis value | 46.5% | 3.4% | 36.2% |

EXAMPLE 3

Synthesis of 3-pyrazolecarbaldehyde-(5-nitro-2-pyridyl)hydrazone (compound 3)

A desired product was obtained in the same manner as in Example 1 by using 3.20 g (20.8 mmol) of 5-nitro-2-pyridylhydrazine and 1.90 g (19.8 mmol) of 3-pyrazolecarbaldehyde.

Yield: 3.92 g (16.9 mmol) [yield rate: 85%]

Melting point: 286° to 287° C.

C-N stretching vibration (IR spectrum) of an azomethine group (—N=CH—): 1600 $cm^{-1}$ (measured by KBr method)

δ value ($^1$H-NMR spectrum) of a hydrogen atom of an azomethine group (—N=CH—): 7.78 ppm (solvent: tetrahydrofuran-$d_8$)

Element analysis: molecular formula: $C_9H_8N_6O_2$ molecular weight: 232.203

|  | Carbon | Hydrogen | Nitrogen |
| --- | --- | --- | --- |
| Calculation value | 46.6% | 3.5% | 36.2% |
| Analysis value | 46.7% | 3.6% | 36.0% |

EXAMPLE 4

Synthesis of 2-thiazolecarbaldehyde-(5-nitro-2-pyridyl)hydrazone (compound 4)

A desired product was obtained in the same manner as in Example 1 by using 3.20 g (20.8 mmol) of 5-nitro-2-pyridylhydrazine and 2.30 g (20.3 mmol) of 2-thiazolecarbaldehyde.

Yield: 3.91 g (15.7 mmol) [yield rate: 77%]

Melting point: 249° to 250° C.

C-N stretching vibration (IR spectrum) of an azomethine group (—N=CH—): 1595 cm$^{-1}$ (measured by KBr method)

δ value ($^1$H-NMR spectrum) of a hydrogen atom of an azomethine group (—N=CH—): 7.64 ppm (solvent: tetrahydrofuran-d$_8$)

Element analysis: molecular formula: $C_9H_7N_5O_2S$ molecular weight: 249.248

|  | Carbon | Hydrogen | Nitrogen | Sulfur |
| --- | --- | --- | --- | --- |
| Calculation value | 43.4% | 2.8% | 28.1% | 12.9% |
| Analysis value | 43.2% | 2.7% | 28.1% | 13.0% |

EXAMPLE 5

Synthesis of 2-pyrrolecarbaldehyde-(5-nitro-2-pyridyl)hydrazone (compound 5)

A desired product was obtained in the same manner as in Example 1 by using 1.54 g (10.0 mmol) of 5-nitro-2-pyridylhydrazine and 1.00 g (10.5 mmol) of 2-pyrrolecarbaldehyde.

Yield: 1.40 g (6.1 mmol) [yield rate: 61%]

Melting point: 218° to 219° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.15 ppm (solvent: tetrahydrofuran-d$_8$)

Element analysis: molecular formula: $C_{10}H_9N_5O_2$ molecular weight: 231.215

|  | Carbon | Hydrogen | Nitrogen |
| --- | --- | --- | --- |
| Calculation value | 52.0% | 3.9% | 30.3% |
| Analysis value | 52.3% | 4.0% | 30.1% |

EXAMPLE 6

Synthesis of 3-indolecarbaldehyde-(5-nitro-2-pyridyl)hydrazone (compound 6)

A desired product was obtained in the same manner as in Example 1 by using 1.54 g (10.0 mmol) of 5-nitro-2-pyridylhydrazine and 1.54 g (10.6 mmol) of 3-indolecarbaldehyde.

Yield: 2.50 g (8.9 mmol) [yield rate: 89%]

Melting point: 304° to 305° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.53 ppm (solvent: tetrahydrofuran-d$_8$)

Element analysis: molecular formula: $C_{14}H_{11}N_5O_2$ molecular weight: 281.275

|  | Carbon | Hydrogen | Nitrogen |
| --- | --- | --- | --- |
| Calculation value | 59.8% | 3.9% | 24.9% |
| Analysis value | 60.0% | 4.0% | 24.7% |

EXAMPLE 7

Synthesis of 2-furancarbaldehyde-(5-nitro-2-pyridyl)hydrazone (compound 7)

A desired product was obtained in the same manner as in Example 1 by using 1.70 g (11.0 mmol) of 5-nitro-2-pyridylhydrazine and 1.0 ml (1.16 g, 12.1 mmol) of 2-furancarbaldehyde.

Yield: 1.52 g (6.6 mmol) [yield rate: 60%]

Melting point: 217° to 218° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.17 ppm (solvent: tetrahydrofuran-d$_8$)

Element analysis: molecular formula: $C_{10}H_8N_4O_3$ molecular weight: 232.199

|  | Carbon | Hydrogen | Nitrogen |
| --- | --- | --- | --- |
| Calculation value | 51.7% | 3.5% | 24.1% |
| Analysis value | 51.4% | 3.5% | 24.2% |

EXAMPLE 8

Synthesis of 2-thiophenecarbaldehyde-(5-nitro-2-pyridyl)hydrazone (compound 8)

A desired product was obtained in the same manner as in Example 1 by using 1.54 g (10.0 mmol) of 5-nitro-2-pyridylhydrazine and 1.0 ml (1.20 g, 10.7 mmol) of 2-thiophenecarbaldehyde.

Yield: 1.79 g (7.2 mmol) [yield rate: 72%]

Melting point: 227° to 228° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.47 ppm (solvent: tetrahydrofuran-d$_8$)

Element analysis: molecular formula: $C_{10}H_8N_4O_2S$ molecular weight: 248.260

|  | Carbon | Hydrogen | Nitrogen | sulfur |
|---|---|---|---|---|
| Calculation value | 48.4% | 3.3% | 22.6% | 12.9% |
| Analysis value | 48.6% | 3.2% | 22.5% | 12.9% |

EXAMPLE 9

Synthesis of benzaldehyde-(5-nitro-2-pyridyl)hydrazone (compound 9)

A desired product was obtained in the same manner as in Example 1 by using 1.70 g (11.0 mmol) of 5-nitro-2-pyridylhydrazine and 1.2 ml (1.25 g, 11.8 mmol) of benzaldehyde.

Yield: 2.10 g (8.7 mmol) [yield rate: 79%]

Melting point: 232° to 233° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.29 ppm (solvent: tetrahydrofuran-d$_8$)

Element analysis: molecular formula: $C_{12}H_{10}N_4O_2$ molecular weight: 242.238

|  | Carbon | Hydrogen | Nitrogen |
|---|---|---|---|
| Calculation value | 59.5% | 4.2% | 23.1% |
| Analysis value | 59.8% | 4.2% | 23.0% |

EXAMPLE 10

Synthesis of 3-pyridinecarbaldehyde-(5-nitro-2-pyridyl)hydrazone (compound 10)

A desired product was obtained in the same manner as in Example 1 by using 1.70 g (11.0 mmol) of 5-nitro-2-pyridylhydrazine and 1.1 ml (1.25 g, 11.7 mmol) of 3-pyridinecarbaldehyde.

Yield: 2.18 g (9.0 mmol) [yield rate: 82%]

Melting point: 293° to 294° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.06 ppm (solvent: tetrahydrofuran-d$_8$)

Element analysis: molecular formula: $C_{11}H_9N_5O_2$ molecular weight: 243.226

|  | Carbon | Hydrogen | Nitrogen |
|---|---|---|---|
| Calculation value | 54.3% | 3.7% | 28.8% |
| Analysis value | 54.1% | 3.8% | 28.8% |

EXAMPLE 11

Synthesis of 4-pyridinecarbaldehyde-(5-nitro-2-pyridyl)hydrazone (compound 11)

A desired product was obtained in the same manner as in Example 1 by using 1.54 g (10.0 mmol) of 5-nitro-2-pyridylhydrazine and 1.0 ml (1.12 g, 10.5 mmol) of 4-pyridinecarbaldehyde.

Yield: 1.76 g (10.0 mmol) [yield rate: 72%]

Melting point: 303° to 304° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.99 ppm (solvent: tetrahydrofuran-d$_8$)

Element analysis: molecular formula: $C_{11}H_9N_5O_2$ molecular weight: 243.226

|  | Carbon | Hydrogen | Nitrogen |
|---|---|---|---|
| Calculation value | 54.3% | 3.7% | 28.8% |
| Analysis value | 54.5% | 3.6% | 28.9% |

EXAMPLE 12

Synthesis of 3-pyridazinecarbadlehyde-(5-nitro-2-pyridyl)hydrazone (compound 12)

A desired product was obtained in the same manner as Example 1 by using 3.20 g (20.8 mmol) of 5-nitro-2-pyridylhydrazine and 2.20 g (20.4 mmol) of 3-pyridazinecarbadlehyde.

Yield: 4.30 g (17.6 mmol) [yield rate: 86%]

Melting point: 275° to 276° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.72 ppm (solvent: tetrahydrofuran-d$_8$)

Element analysis: molecular formula: $C_{10}H_8N_6O_2$ molecular weight: 244.214

|  | Carbon | Hydrogen | Nitrogen |
|---|---|---|---|
| Calculation value | 49.2% | 3.3% | 34.4% |
| Analysis value | 49.1% | 3.3% | 34.4% |

EXAMPLE 13

Synthesis of 2-pyrimidinecarbaldehyde-(5-nitro-2-pyridyl)hydrazone (compound 13)

A desired product was obtained in the same manner as in Example 1 by using 3.20 g (20.8 mmol) of 5-nitro-2-pyridylhydrazine and 2.20 g (20.4 mmol) of 2-pyrimidinecarbaldehyde.

Yield: 3.60 g (14.7 mmol) [yield rate: 72%]

Melting point: 288° to 289° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.80 ppm (solvent: tetrahydrofuran-d$_8$)

Element analysis: molecular formula: $C_{10}H_8N_6O_2$ molecular weight: 244.214

|                   | Carbon | Hydrogen | Nitrogen |
|-------------------|--------|----------|----------|
| Calculation value | 49.2%  | 3.3%     | 34.4%    |
| Analysis value    | 49.4%  | 3.2%     | 34.5%    |

EXAMPLE 14

Synthesis of 4-pyrimidinecarbaldehyde-(5-nitro-2-pyridyl)hydrazone (compound 14)

A desired product was obtained in the same manner as in Example 1 by using 3.20 g (20.8 mmol) of 5-nitro-2-pyridylhydrazine and 2.2 g (20.4 mmol) of 4-pyrimidinecarbaldehyde.

Yield: 4.00 g (16.4 mmol) [yield rate: 80%]

Melting point: 290° to 291° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.78 ppm (solvent: tetrahydrofuran-d$_8$)

Element analysis: molecular formula: $C_{10}H_8N_6O_2$ molecular weight: 244.214

|                   | Carbon | Hydrogen | Nitrogen |
|-------------------|--------|----------|----------|
| Calculation value | 49.2%  | 3.3%     | 34.4%    |
| Analysis value    | 49.2%  | 3.3%     | 34.3%    |

EXAMPLE 15

Synthesis of 2-pyrazinecarbaldehyde-(5-nitro-2-pyridyl)hydrazone (compound 15)

3.20 g (20.8 mmol) of 5-nitro-2-pyridylhydrazine and 4.60 g (20.3 mmol) of 2-pyrazinecarbaldehyde-(4-dimethylamino)anil were dissolved in 200 ml of ethanol. To this mixture, 20 ml of concentrated hydrochloric acid was added and heated under reflux for 2 hours while being stirred. After the resultant reaction mixture was allowed to stand still overnight, precipitated coarse crystals were filtrated by the suction-filtration. The obtained coarse crystals were recrystallized from a hot ethanol solution to obtain a desired product.

Yield: 3.10 g (12.7 mmol) [yield rate: 62%]

Melting point: 271° to 272° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.74 ppm (solvent: tetrahydrofuran-d$_8$)

Element analysis: molecular formula: $C_{10}H_8N_6O_2$ molecular weight: 244.214

|                   | Carbon | Hydrogen | Nitrogen |
|-------------------|--------|----------|----------|
| Calculation value | 49.2%  | 3.3%     | 34.4%    |
| Analysis value    | 49.5%  | 3.2%     | 34.2%    |

EXAMPLE 16

Synthesis of 1-phthalazinecarbaldehyde-(5-nitro-2-pyridyl)hydrazone (compound 16)

A desired product was obtained in the same manner as in Example 15 by using 3.20 g (20.8 mmol) of 5-nitro-2-pyridylhydrazine and 5.60 g (20.3 mmol) of 1-phthalazinecarbaldehyde-(4-dimethylamino)anil.

Yield: 5.00 g (17.0 mmol) [yield rate: 84%]

Melting point: 292° to 293° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.60 ppm (solvent: tetrahydrofuran-d$_8$)

Element analysis: molecular formula: $C_{14}H_{10}N_6O_2$ molecular weight: 294.274

|                   | Carbon | Hydrogen | Nitrogen |
|-------------------|--------|----------|----------|
| Calculation value | 57.1%  | 3.4%     | 28.6%    |
| Analysis value    | 57.2%  | 3.4%     | 28.5%    |

EXAMPLE 17

Synthesis of 2-quinazolinecarbaldehyde-(5-nitro-2-pyridyl)hydrazone (compound 17)

A desired product was obtained in the same manner as in Example 15 by using 3.20 g (20.8 mmol) of 5-nitro-2-pyridylhydrazine and 5.60 g (20.3 mmol) of 2-quinazolinecarbaldehyde-(4-dimethylamino)anil.

Yield: 5.50 g (18.7 mmol) [yield rate: 92%]

Melting point: 299° to 300° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.65 ppm (solvent: tetrahydrofuran-d$_8$)

Element analysis: molecular formula: $C_{14}H_{10}N_6O_2$ molecular weight: 294.274

|  | Carbon | Hydrogen | Nitrogen |
| --- | --- | --- | --- |
| Calculation value | 57.1% | 3.4% | 28.6% |
| Analysis value | 57.3% | 3.5% | 28.6% |

EXAMPLE 18

Synthesis of 2-benzothiazolecarbaldehyde-(5-nitro-2-pyridyl)hydrazone (compound 18)

A desired product was obtained in the same manner as in Example 1 by using 3.20 g (20.8 mmol) of 5-nitro-2-pyridylhydrazine and 3.30 g (20.2 mmol) of 2-benzothiazolecarbaldehyde.

Yield: 5.90 g (19.7 mmol) [yield rate: 97%]

Melting point: 306° to 307° C.

C-N stretching vibration (IR spectrum) of an azomethine group (—N=CH—): 1595 $cm^{-1}$ (measured by KBr method)

$\delta$ value ($^1$H-NMR spectrum) of a hydrogen atom of an azomethine group (—N=CH—): 7.68 ppm (solvent: tetrahydrofuran-$d_8$)

Element analysis: molecular formula: $C_{13}H_9N_5O_2S$ molecular weight: 299.308

|  | Carbon | Hydrogen | Nitrogen | Sulfur |
| --- | --- | --- | --- | --- |
| Calculation value | 52.2% | 3.0% | 23.4% | 10.7% |
| Analysis value | 52.1% | 3.0% | 23.2% | 10.8% |

EXAMPLE 19

Synthesis of 2-benzimidazolecarbaldehyde-(5-nitro-2-pyridyl)hydrazone (compound 19)

A desired product was obtained in the same manner as in Example 1 by using 3.20 g (20.8 mmol) of 5-nitro-2-pyridylhydrazine and 2.90 g (19.8 mmol) of 2-benzimidazolecarbaldehyde.

Yield: 4.80 g (17.0 mmol) [yield rate: 86%]

Melting point: 310° to 311° C.

C-N stretching vibration (IR spectrum) of an azomethine group (—N=CH—): 1600 $cm^{-1}$ (measured by KBr method)

$\delta$ value ($^1$H-NMR spectrum) of a hydrogen atom of an azomethine group (—N=CH—): 7.92 ppm (solvent: tetrahydrofuran-$d_8$)

Element analysis: molecular formula: $C_{13}H_{10}N_6O_2$ molecular weight: 282.263

|  | Carbon | Hydrogen | Nitrogen |
| --- | --- | --- | --- |
| Calculation value | 55.3% | 3.6% | 29.8% |
| Analysis value | 55.5% | 3.5% | 29.8% |

EXAMPLE 20

Synthesis of 1-methyl-2-benzimidazolecarbaldehyde-(5-nitro-2-pyridyl)hydrazone (compound 20)

A desired product was obtained in the same manner as in Example 1 by using 3.20 g (20.8 mmol) of 5-nitro-2-pyridylhydrazine and 3.20 g (20.0 mmol) of 1-methyl-2-benzimidazolecarbaldehyde.

Yield: 4.90 g (16.5 mmol) [yield rate: 83%]

Melting point: 302° to 303° C.

C-N stretching vibration (IR spectrum) of an azomethine group (—N=CH—): 1600 $cm^{-1}$ (measured by KBr method)

$\delta$ value ($^1$H-NMR spectrum) of a hydrogen atom of an azomethine group (—N=CH—): 7.88 ppm (solvent: tetrahydrofuran-$d_8$)

Element analysis: molecular formula: $C_{13}H_{10}N_6O_2$ molecular weight: 296.290

|  | Carbon | Hydrogen | Nitrogen |
| --- | --- | --- | --- |
| Calculation value | 56.8% | 4.1% | 28.4% |
| Analysis value | 56.6% | 4.0% | 28.5% |

EXAMPLE 21

Synthesis of 2-quinolinecarbaldehyde-(5-nitro-2-pyridyl)hydrazone (compound 21)

A desired product was obtained in the same manner as in Example 1 by using 3.20 g (20.8 mmol) of 5-nitro-2-pyridylhydrazine and 3.10 g (19.7 mmol) of 2-quinolinecarbaldehyde.

Yield: 5.50 g (18.8 mmol) [yield rate: 95%]

Melting point: 320° to 321° C.

C-N stretching vibration (IR spectrum) of an azomethine group (—N=CH—): 1600 $cm^{-1}$ (measured by KBr method)

$\delta$ value ($^1$H-NMR spectrum) of a hydrogen atom of an azomethine group (—N=CH—): 8.24 ppm (solvent: tetrahydrofuran-$d_8$)

Element analysis: molecular formula: $C_{15}H_{11}N_5O_2$ molecular weight: 293.286

|  | Carbon | Hydrogen | Nitrogen |
| --- | --- | --- | --- |
| Calculation value | 61.4% | 3.8% | 23.9% |
| Analysis value | 61.2% | 3.9% | 23.8% |

EXAMPLE 22

Synthesis of 1-isoquinolinecarbaldehyde-(5-nitro-2-pyridyl)hydrazone (compound 22)

A desired product was obtained in the same manner as in Example 1 by using 3.20 g (20.8 mmol) of 5-nitro-2-pyridylhydrazine and 3.10 g (19.7 mmol) of 1-isoquinolinecarbaldehyde.

Yield: 4.80 g (16.4 mmol) [yield rate: 83%]

Melting point: 303° to 304° C.

C-N stretching vibration (IR spectrum) of an azomethine group (—N=CH—): 1595 cm$^{-1}$ (measured by KBr method)

δ value ($^1$H-NMR spectrum) of a hydrogen atom of an azomethine group (—N=CH—): 7.92 ppm (solvent: tetrahydrofuran-d$_8$)

Element analysis: molecular formula: $C_{15}H_{11}N_5O_2$ molecular weight: 293.286

|  | Carbon | Hydrogen | Nitrogen |
|---|---|---|---|
| Calculation value | 61.4% | 3.8% | 23.9% |
| Analysis value | 61.0% | 3.7% | 24.1% |

EXAMPLE 23

Synthesis of 3-isoquinolinecarbaldehyde-(5-nitro-2-pyridyl)hydrazone (compound 23)

A desired product was obtained in the same manner as in Example 1 by using 3.20 g (20.8 mmol) of 5-nitro-2-pyridylhydrazine and 3.10 g (19.7 mmol) of 3-isoquinolinecarbaldehyde.

Yield: 5.10 g (17.4 mmol) [yield rate: 88%]

Melting point: 317° to 318° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.81 ppm (solvent: tetrahydrofuran-d$_8$)

Element analysis: molecular formula: $C_{15}H_{11}N_5O_2$ molecular weight: 293.286

|  | Carbon | Hydrogen | Nitrogen |
|---|---|---|---|
| Calculation value | 61.4% | 3.8% | 23.9% |
| Analysis value | 61.6% | 3.8% | 23.7% |

EXAMPLE 24

Synthesis of 6-phenanthridinecarbaldehyde-(5-nitro-2-pyridyl)hydrazone (compound 24)

A desired product was obtained in the same manner as in Example 1 by using 3.20 g (20.8 mmol) of 5-nitro-2-pyridylhydrazine and 4.20 g (20.3 mmol) of 6-phenanthridinecarbaldehyde.

Yield: 6.40 g (18.6 mmol) [yield rate: 92%]

Melting point: 296° to 297° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 8.09 ppm (solvent: tetrahydrofuran-d$_8$)

Element analysis: molecular formula: $C_{19}H_{13}N_5O_2$ molecular weight: 343.346

|  | Carbon | Hydrogen | Nitrogen |
|---|---|---|---|
| Calculation value | 66.5% | 3.8% | 20.4% |
| Analysis value | 66.2% | 3.8% | 20.5% |

EXAMPLE 25

Synthesis of bis(2-thiazolyl)methanone-(5-nitro-2-pyridyl)hydrazone (compound 25)

A desired product was obtained in the same manner as in Example 1 by using 3.20 g (20.8 mmol) of 5-nitro-2-pyridylhydrazine and 3.90 g (19.9 mmol) of bis(2-thiazolyl)ketone.

Yield: 5.70 g (17.2 mmol) [yield rate: 86%]

Melting point: 262° to 263° C.

C-N stretching vibration (IR spectrum) of an azomethine group (—N=C<): 1595 cm$^{-1}$ (measured by KBr method)

Element analysis: molecular formula: $C_{12}H_8N_6O_2S_2$ molecular weight: 332.356

|  | Carbon | Hydrogen | Nitrogen | Sulfur |
|---|---|---|---|---|
| Calculation value | 43.4% | 2.4% | 25.3% | 19.3% |
| Analysis value | 43.3% | 2.5% | 25.2% | 19.3% |

EXAMPLE 26

Synthesis of bis(3-pyridazinyl)methanone-(5-nitro-2-pyridyl)hydrazone (compound 26)

A desired product was obtained in the same manner as in Example 1 by using 3.20 g (20.8 mmol) of 5-nitro-2-pyridylhydrazine and 3.70 g (19.9 mmol) of bis(3-pyridazinyl) ketone.

Yield: 6.00 g (18.6 mmol) [yield rate: 94%]

Melting point: 286° to 287° C.

C-N stretching vibration (IR spectrum) of an azomethine group (—N=C<): 1600 cm$^{-1}$ (measured by KBr method)

Element analysis: molecular formula: $C_{14}H_{10}N_8O_2$ molecular weight: 322.288

|  | Carbon | Hydrogen | Nitrogen |
|---|---|---|---|
| Calculation value | 52.2% | 3.1% | 34.8% |
| Analysis value | 52.4% | 3.2% | 34.7% |

EXAMPLE 27

Synthesis of 2-pyridinecarbaldehyde-(5-cyano-2-pyridyl)hydrazone (compound 27)

A desired product was obtained in the same manner as in Example 1 by using 2.70 g (20.1 mmol) of 5-cyano-2-pyridylhydrazine and 2.0 ml (2.25 g 21.0 mmol) of 2-pyridinecarbaldehyde.

Yield: 3.40 g (15.2 mmol) [yield rate: 76%]

Melting point: 242° to 243° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.84 ppm (solvent: tetrahydrofuran-d$_8$)

Element analysis: molecular formula: $C_{12}H_9N_5$ molecular weight: 223.239

|  | Carbon | Hydrogen | Nitrogen |
|---|---|---|---|
| Calculation value | 64.6% | 4.1% | 31.4% |
| Analysis value | 64.4% | 4.0% | 31.6% |

EXAMPLE 28

Synthesis of 2-pyridinecarbaldehyde-(5-trifluoromethyl-2-pyridyl)hydrazone (compound 28)

A desired product was obtained in the same manner as in Example 1 by using 3.60 g (20.3 mmol) of 5-trifluoromethyl-2-pyridylhydrazine and 2.0 ml (2.25 g, 21.0 mmol) of 2-pyridinecarbaldehyde.

Yield: 3.20 g (12.0 mmol) [yield rate: 59%]

Melting point: 208° to 209° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.78 ppm (solvent: tetrahydrofuran-d$_8$)

Element analysis: molecular formula: $C_{12}H_9F_3N_4$ molecular weight: 266.226

|  | Carbon | Hydrogen | Fluorine | Nitrogen |
|---|---|---|---|---|
| Calculation value | 54.1% | 3.4% | 21.4% | 21.1% |
| Analysis value | 54.2% | 3.5% | 21.3% | 21.0% |

EXAMPLE 29

Synthesis of 2-pyridinecarbaldehyde-(3-chloro-5-trifluoromethyl-2-pyridyl)hydrazone (compound 29)

A desired product was obtained in the same manner as in Example 1 by using 4.30 g (20.3 mmol) of 3-chloro-5-trifluoromethyl-2-pyridylhydrazine and 2.0 ml (2.25 g, 21.0 mmol) of 2-pyridinecarbaldehyde.

Yield: 3.20 g (10.6 mmol) [yield rate: 52%]

Melting point: 225° to 226° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.75 ppm (solvent: tetrahydrofuran-d$_8$)

Element analysis: molecular formula: $C_{12}H_8Cl_1F_3N_4$ molecular weight: 300.671

|  | Carbon | Hydrogen | Chlorine | Fluorine | Nitrogen |
|---|---|---|---|---|---|
| Calculation value | 47.9% | 2.7% | 11.8% | 19.0% | 18.6% |
| Analysis value | 48.1% | 2.6% | 11.8% | 18.9% | 18.6% |

EXAMPLE 30

Synthesis of 2-thiazolecarbaldehyde-(5-cyano-2-pyridyl)hydrazone (compound 30)

A desired product was obtained in the same manner as in Example 1 by using 2.70 g (20.1 mmol) of 5-cyano-2-pyridylhydrazine and 2.40 g (21.2 mmol) of 2-thiazolecarbaldehyde.

Yield: 3.40 g (14.8 mmol) [yield rate: 74%]

Melting point: 221° to 222° C.

C-N stretching vibration (IR spectrum) of an azomethine group (—N=CH—): 1595 cm$^{-1}$ (measured by KBr method)

δ value ($^1$H-NMR spectrum) of a hydrogen atom of an azomethine group (—N=CH—): 7.79 ppm (solvent: tetrahydrofuran-d$_8$)

Element analysis: molecular formula: $C_{10}H_7N_5S$ molecular weight: 229.261

|  | Carbon | Hydrogen | Nitrogen | Sulfur |
|---|---|---|---|---|
| Calculation value | 52.4% | 3.1% | 30.6% | 14.0% |
| Analysis value | 52.5% | 3.0% | 30.5% | 14.0% |

EXAMPLE 31

Synthesis of 2-thiazolecarbaldehyde-(5-trifluoromethyl-2-pyridyl)hydrazone (compound 31)

A desired product was obtained in the same manner as in Example 1 by using 3.60 g (20.3 mmol) of 5-trifluoromethyl-2-pyridylhydrazine and 2.40 g (21.2 mmol) of 2-thiazolecarbaldehyde.

Yield: 2.80 g (10.3 mmol) [yield rate: 51%]

Melting point: 189° to 190° C.

C-N stretching vibration (IR spectrum) of an azomethine group (—N=CH—): 1595 cm$^{-1}$ (measured by KBr method)

δ value ($^1$H-NMR spectrum) of a hydrogen atom of an azomethine group (—N=CH—): 7.76 ppm (solvent: tetrahydrofuran-d$_8$)

Element analysis: molecular formula: $C_{10}H_7F_3N_4S$ molecular weight: 272.248

|  | Carbon | Hydrogen | Fluorine | Nitrogen | Sulfur |
|---|---|---|---|---|---|
| Calculation value | 44.1% | 2.6% | 20.9% | 20.6% | 11.8% |
| Analysis value | 44.2% | 2.6% | 21.0% | 20.5% | 11.7% |

EXAMPLE 32

Synthesis of 3-pyridazinecarbadlehyde-(5-cyano-2-pyridyl)hydrazone (compound 32)

A desired product was obtained in the same manner as in Example 1 by using 2.70 g (20.1 mmol) of 5-cyano-2-pyridylhydrazine and 2.30 g (21.3 mmol) of 3-pyridazinecarbadlehyde.

Yield: 3.60g (16.1 mmol) [yield rate: 80%]

Melting point: 241° to 242° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.86 ppm (solvent: tetrahydrofuran-d$_8$)

Element analysis: molecular formula: C$_{11}$H$_8$N$_6$ molecular weight: 224.227

|  | Carbon | Hydrogen | Nitrogen |
|---|---|---|---|
| Calculation value | 58.9% | 3.6% | 37.5% |
| Analysis value | 59.1% | 3.6% | 37.3% |

EXAMPLE 33

Synthesis of 3-pyridazinecarbadlehyde-(5-trifluoromethyl-2-pyridyl)hydrazone (compound 33)

A desired product was obtained in the same manner as in Example 1 by 31 using 3.60 g (20.3 mmol) of 5-trifluoromethyl-2-pyridylhydrazine and 2.30 (21.3 mmol) of 3-pyridazinecarbadlehyde.

Yield: 3.10 g (11.6 mmol) [yield rate: 57%]

Melting point: 206° to 207° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.78 ppm (solvent: tetrahydrofuran-d$_8$)

Element analysis: molecular formula: C$_{11}$H$_8$F$_3$N$_5$ molecular weight: 267.214

|  | Carbon | Hydrogen | Fluorine | Nitrogen |
|---|---|---|---|---|
| Calculation value | 49.4% | 3.0% | 21.3% | 26.2% |
| Analysis value | 49.3% | 3.1% | 21.3% | 26.3% |

EXAMPLE 34

Synthesis of 2-benzothiazolecarbaldehyde-(5-cyano-2-pyridyl)hydrazone (compound 34)

A desired product was obtained in the same manner as in Example 1 by using 2.70 g (20.1 mmol) of 5-cyano-2-pyridylhydrazine and 3.40 g (20.8 mmol) of 2-benzothiazolecarbaldehyde.

Yield: 4.70 g (16.8 mmol) [yield rate: 84%]

Melting point: 253° to 254° C.

C-N stretching vibration (IR spectrum) of an azomethine group (—N=CH—): 1595 cm$^{-1}$ (measured by KBr method)

δ value ($^1$H-NMR spectrum) of a hydrogen atom of an azomethine group (—N=CH—): 7.75 ppm (solvent: tetrahydrofuran-d$_8$)

Element analysis: molecular formula: C$_{14}$H$_9$N$_5$S molecular weight: 279.321

|  | Carbon | Hydrogen | Nitrogen | Sulfur |
|---|---|---|---|---|
| Calculation value | 60.2% | 3.3% | 25.1% | 11.5% |
| Analysis value | 60.5% | 3.2% | 24.9% | 11.4% |

EXAMPLE 35

Synthesis of bis(2-pyridyl)methanone-(5-cyano-2-pyridyl)hydrazone (compound 35)

A desired product was obtained in the same manner as in Example 1 by using 2.70 g (20.1 mmol) of 5-cyano-2-pyridylhydrazine and 3.90 g (21.2 mmol) of bis(2-pyridyl)ketone.

Yield: 4.90 g (16.3 mmol) [yield rate: 81%]

Melting point: 256° to 257° C.

C-N stretching vibration (IR spectrum) of an azomethine group (—N=C<): 1600 cm$^{-1}$ (measured by KBr method)

Element analysis: molecular formula: C$_{17}$H$_{12}$N$_6$ molecular weight: 300.325

|  | Carbon | Hydrogen | Nitrogen |
|---|---|---|---|
| Calculation value | 68.0% | 4.0% | 28.0% |
| Analysis value | 68.1% | 4.1% | 27.8% |

EXAMPLE 36

Synthesis of 2-pyridinecarbaldehyde-(3,5-dinitro-2-pyridyl)hydrazone (compound 36)

A desired product was obtained in the same manner as in Example 1 by using 4.00 g (20.1 mmol) of 3,5-dinitro-2-pyridylhydrazine and 2.0 ml (2.25 g, 21.0 mmol) of 2-pyridinecarbaldehyde.

Yield: 5.30 g (18.4 mmol) [yield rate: 91%]

Melting point: 299° to 300° C.

C-N stretching vibration (IR spectrum) of an azomethine group (—N=CH—): 1600 cm$^{-1}$ (measured by KBr method)

δ value ($^1$H-NMR spectrum) of a hydrogen atom of an azomethine group (—N=CH—): 7.64 ppm (solvent: tetrahydrofuran-d$_8$)

Element analysis: molecular formula: C$_{11}$H$_8$N$_6$O$_4$ molecular weight: 288.223

|  | Carbon | Hydrogen | Nitrogen |
|---|---|---|---|
| Calculation value | 45.8% | 2.8% | 29.2% |
| Analysis value | 45.9% | 2.8% | 29.1% |

EXAMPLE 37

Synthesis of bis(2-pyridyl)methanone-(3, 5 dinitro-2-pyridyl)hydrazone (compound 37)

A desired product was obtained in the same manner as in Example 1 by using 4.00 g (20.1 mmol) of 3,5-dinitro-2-pyridylhydrazine and 3.90 g (21.2 mmol) of bis(2-pyridyl)ketone.

Yield: 6.90 g (18.9 mmol) [yield rate: 94%]

Melting point: 309° to 310° C.

C-N stretching vibration (IR spectrum) of an azomethine group (—N=C<): 1600 cm$^{-1}$ (measured by KBr method)

Element analysis: molecular formula: $C_{16}H_{11}N_7O_4$ molecular weight: 365.309

|                   | Carbon | Hydrogen | Nitrogen |
|-------------------|--------|----------|----------|
| Calculation value | 52.6%  | 3.0%     | 26.8%    |
| Analysis value    | 52.4%  | 3.1%     | 26.9%    |

EXAMPLE 38

Synthesis of bis(2-pyridyl)methanone-(5-nitro-2-pyridyl)hydrazone (compound 38)

A desired product was obtained in the same manner as in Example 1 by using 3.20 g (20.8 mmol) of 5-nitro-2-pyridylhydrazine and 3.70 g (20.1 mmol) of bis(2-pyridyl)ketone.

Yield: 5.80 g (18.1 mmol) [yield rate: 90%]

Melting point: 289° to 290° C.

C-N stretching vibration (IR spectrum) of an azomethine group (—N=C<): 1600 cm$^{-1}$ (measured by KBr method)

Element analysis: molecular formula: $C_{16}H_{12}N_6O_2$ molecular weight: 320.312

|                   | Carbon | Hydrogen | Nitrogen |
|-------------------|--------|----------|----------|
| Calculation value | 60.0%  | 3.8%     | 26.2%    |
| Analysis value    | 60.3%  | 3.8%     | 26.1%    |

(B) Determination of nonlinear optical effect

A secondary nonlinear optical effect was analyzed by the so-called powder method with respect to hydrazone compounds of Examples 1–4 (Compounds 1–4), Examples 12–19 (Compounds 12–19), Examples 20–26 (Compounds 20–26), Examples 27–35 (Compounds 27–35), Examples 36–38 (Compounds 36–38) and urea (Comparative Example 1). To be more specific, crystal powder of each compound was pulverized in an agate mortar and classified with a sieve to prepare powder having a particle diameter in the range of 100 to 150 μm. The resultant powder was placed between slide-glass plates, thereby obtaining a test sample. Onto the test sample, a fundamental wave (wavelength=1.064 μm) of an Nd-YAG laser was irradiated and intensity of a second harmonic generation (SHG) component of reflection light was measured. The intensity of the second harmonic generation of each sample is standardized on the basis of that of the second harmonic generation of urea powder (Comparative Example 1). The results are shown in Tables 1 to 5.

As is apparent from Tables 1 to 5, the crystals of Compounds 1–4 generate SHG ten-twenty to several-ten times as large as that of urea (Comparative Example 1). It can be also found that crystals of Compounds 12–19, 20–26, 27–35, and 36–38 generate SHG several-ten times as large as that of urea (Comparative Example 1). From the foregoing, it is apparent that the hydrazone compounds of the present invention have excellent nonlinearity. In particular, Compounds 1–3 exhibit excellent solubility in a solvent, so that the crystals thereof were easily prepared.

TABLE 1

| Compound  | Structure of Compound | SHG strength (ratio to urea) |
|-----------|-----------------------|------------------------------|
| Example 1 Compound 1 | | 18 |
| Example 2 Compound 2 | | 32 |
| Example 3 Compound 3 | | 46 |

TABLE 1-continued

| | Compound | Structure of Compound | SHG strength (ratio to urea) |
|---|---|---|---|
| Example 4 | Compound 4 | (5-nitropyridin-2-yl)hydrazone of thiazole-2-carbaldehyde | 80 |
| Comparative Example 1 | Urea | H₂N—C(=O)—NH₂ | 1 |

TABLE 2

| | Compound | Structure of Compound | SHG strength (ratio to urea) |
|---|---|---|---|
| Example 12 | Compound 12 | (5-nitropyridin-2-yl)hydrazone of pyridazine-3-carbaldehyde | 75 |
| Example 13 | Compound 13 | (5-nitropyridin-2-yl)hydrazone of pyrimidine-2-carbaldehyde | 52 |
| Example 14 | Compound 14 | (5-nitropyridin-2-yl)hydrazone of pyrimidine-4-carbaldehyde | 60 |
| Example 15 | Compound 15 | (5-nitropyridin-2-yl)hydrazone of pyrazine-2-carbaldehyde | 28 |
| Example 16 | Compound 16 | (5-nitropyridin-2-yl)hydrazone of phthalazine-1-carbaldehyde | 47 |
| Example 17 | Compound 17 | (5-nitropyridin-2-yl)hydrazone of isoquinoline-3-carbaldehyde | 62 |
| Example 18 | Compound 18 | (5-nitropyridin-2-yl)hydrazone of benzothiazole-2-carbaldehyde | 75 |

TABLE 2-continued

| | Compound | Structure of Compound | SHG strength (ratio to urea) |
|---|---|---|---|
| Example 19 | Compound 19 | [structure: 5-nitro-2-pyridyl-NH-N=C(H)-NH-(2-pyridyl-phenyl fused)] | 28 |
| Comparative Example 1 | Urea | H₂N—C(=O)—NH₂ | 1 |

TABLE 3

| | Compound | Structure of Compound | SHG strength (ratio to urea) |
|---|---|---|---|
| Example 20 | Compound 20 | [structure with CH₃ substituent on N] | 46 |
| Example 21 | Compound 21 | [structure with naphthyl/quinolinyl group] | 57 |
| Example 22 | Compound 22 | [structure with isoquinolinyl group] | 38 |
| Example 23 | Compound 23 | [structure with isoquinolinyl group, different isomer] | 52 |
| Example 24 | Compound 24 | [structure with phenanthridinyl group] | 40 |
| Example 25 | Compound 25 | [structure with thiazolyl groups] | 50 |

TABLE 3-continued

| | Compound | Structure of Compound | SHG strength (ratio to urea) |
|---|---|---|---|
| Example 26 | Compound 26 | (2-pyridyl)-C(=N-NH-(5-nitro-2-pyridyl))-(2-pyrazinyl) | 48 |
| Comparative Example 1 | Urea | H₂N—C(=O)—NH₂ | 1 |

TABLE 4

| | Compound | Structure of Compound | SHG strength (ratio to urea) |
|---|---|---|---|
| Example 27 | Compound 27 | (5-cyano-2-pyridyl)-NH-N=CH-(2-pyridyl) | 35 |
| Example 28 | Compound 28 | (5-trifluoromethyl-2-pyridyl)-NH-N=CH-(2-pyridyl) | 28 |
| Example 29 | Compound 29 | (3-chloro-5-trifluoromethyl-2-pyridyl)-NH-N=CH-(2-pyridyl) | 32 |
| Example 30 | Compound 30 | (5-cyano-2-pyridyl)-NH-N=C(2-thienyl)-(2-pyridyl) substituent | 46 |
| Example 31 | Compound 31 | (5-trifluoromethyl-2-pyridyl)-NH-N=C(2-thienyl)-(2-pyridyl) | 33 |
| Example 32 | Compound 32 | (5-cyano-2-pyridyl)-NH-N=CH-(2-pyrazinyl) | 38 |
| Example 33 | Compound 33 | (5-trifluoromethyl-2-pyridyl)-NH-N=CH-(2-pyrazinyl) | 32 |

TABLE 4-continued

| Compound | | Structure of Compound | SHG strength (ratio to urea) |
|---|---|---|---|
| Example 34 | Compound 34 | (structure shown) | 52 |
| Example 35 | Compound 35 | (structure shown) | 28 |
| Comparative Example 1 | Urea | $H_2N-C(=O)-NH_2$ | 1 |

TABLE 5

| Compound | | Structure of Compound | SHG strength (ratio to urea) |
|---|---|---|---|
| Example 36 | Compound 36 | (structure shown) | 52 |
| Example 37 | Compound 37 | (structure shown) | 44 |
| Example 38 | Compound 38 | (structure shown) | 56 |
| Comparative Example 1 | Urea | $H_2N-C(=O)-NH_2$ | 1 |

Furthermore, visible-ultraviolet transmission spectra of hydrazone compounds of Examples 27, 28 and 36 were determined using a 0.001M ethanol solution. The results are shown in FIG. 1. As is apparent from FIG. 1, the light absorption band of hydrazone compounds 27 and 28 (an electron attractive group $R^1$ of the formula (1) is a cyano group or a trifluoromethyl group) shifts to a short wavelength zone in comparison with that of hydrazone compound 36 ($R^1$ is a nitro group). As a result, there is no light absorption zone in the visible light range of hydrazone compounds 27 and 28, so that light transmissivity is found to be high even in a blue color wavelength range. It is found that nonlinear optical material comprising hydrazone compounds 27 and 28 can generate a harmonic wave efficiently in the visible light range without disturbance of internal absorption.

Hydrazone compounds 35 to 38, all exhibit a melting point particularly as high as 250° C. or more. These compounds have two nitro groups which bind to the pyridine ring serving as a π electron system skeleton and/or two 2-pyridyl groups which bind to the hydrazone carbon. Hence, the nonlinear optical materials comprising hydrazone compounds represented by the formulas (2) and (3) are particularly excellent in heat resistance.

(C) Determination of optical absorption properties of organic metal complex

Light absorption properties were analyzed by absorption spectrophotometry, as mentioned below, with respect to a nickel (II) complex of Compounds 1–4, 2–19, 20–26, 27–35, 36–38 and cuprizone (Comparative Example 2).

Ethanol solutions (20 ml), each containing $2.5\times10^{-4}$M Compounds 1–4 were placed in 50 ml volumetric flasks (final concentration: $1\times10^{-4}$ mol). To these solutions, 2 ml of a 8.056 ppm ($1.373\times10^{-4}$M) nickel chloride (II) aqueous solution was added (final concentration: $5.491\times10^{-6}$M). Further, a pH buffer solution (pH7: 1M Tris(hydroxymethyl)aminomethan-hydrochloric acid base buffer solution; pH9: 1M ammonia-hydrochloric acid base buffer solution) was added thereto, and diluted with ion-exchanged water. After the reaction mixture was allowed to stand-still for one hour, a visible light absorption spectrum of each test sample was determined using a automatic spectrophotometer. As a control sample, a reagent blank solution which is same as the test solution except that the nickel chloride (II) aqueous solution was eliminated, was employed. The results are shown in Table 6.

1,4-dioxane solutions (20 ml), each containing $2.5\times10^{-4}$M Compounds 12–19, 20–26, 27–35 and 36–38 were placed in 50 ml volumetric flasks (final concentration $1\times10^{-4}$ mol). To these solutions, 2 ml of a 8.056 ppm ($1.373\times10^{-4}$M) nickel chloride (II) aqueous solution was added (final concentration: $5.491\times10^{-6}$M). Further, the same pH buffer solution as used in the above was added thereto and diluted with ion-exchanged water. After the reaction mixture was allowed to stand-still for one hour, a visible light absorption spectrum of each test sample was determined using an automatic spectrophotometer. As a control sample, the reagent blank solution which is same as the test solution except that the nickel chloride (II) aqueous solution is eliminated, was employed. The results are shown in Tables 7 to 10.

As is apparent form Tables 6 to 10, it is demonstrated that nickel (II) complexes of hydrazone compounds 1–4, 12–19, 20–26, 27–35, 36–38 have a molar absorptivity several to ten-twenty times as large as that of the nickel (II) complex of cuprizone of Comparative Example 2. Since the hydrazone compounds of the present invention form a metal complex by coordinating to specific metal ions, as evidenced from these results, it is demonstrated that they are excellent highly-sensitive coloring chelation agents.

TABLE 6

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
| --- | --- | --- | --- | --- |
| Example 1 | Compound 1 | | 478 ($6.99\times10^4$) | 478 ($7.10\times10^4$) |
| Example 2 | Compound 2 | | 471 ($5.11\times10^4$) | 471 ($8.01\times10^4$) |
| Example 3 | Compound 3 | | 465 ($5.96\times10^4$) | 465 ($6.53\times10^4$) |
| Example 4 | Compound 4 | | 467 ($1.05\times10^5$) | 467 ($1.05\times10^5$) |

TABLE 6-continued

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Comparative Example 2 | Cuprizone | (structure) | 330 ($7.0 \times 10^3$) | 330 ($9.0 \times 10^3$) |

TABLE 7

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 12 | Compound 12 | (structure) | 480 ($1.10 \times 10^5$) | 480 ($1.10 \times 10^5$) |
| Example 13 | Compound 13 | (structure) | 478 ($6.50 \times 10^4$) | 478 ($1.05 \times 10^5$) |
| Example 14 | Compound 14 | (structure) | 482 ($6.50 \times 10^4$) | 482 ($1.10 \times 10^5$) |
| Example 15 | Compound 15 | (structure) | 475 ($4.20 \times 10^4$) | 475 ($1.00 \times 10^5$) |
| Example 16 | Compound 16 | (structure) | 500 ($1.15 \times 10^5$) | 500 ($1.15 \times 10^5$) |
| Example 17 | Compound 17 | (structure) | 505 ($5.80 \times 10^4$) | 505 ($1.10 \times 10^5$) |
| Example 18 | Compound 18 | (structure) | 512 ($1.20 \times 10^5$) | 512 ($1.13 \times 10^5$) |

TABLE 7-continued

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 19 | Compound 19 | (structure) | 493 ($1.18 \times 10^5$) | 493 ($1.15 \times 10^5$) |
| Comparative Example 2 | Cuprizone | (structure) | 330 ($7.0 \times 10^3$) | 330 ($9.0 \times 10^3$) |

TABLE 8

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 20 | Compound 20 | (structure) | 491 ($1.19 \times 10^5$) | 491 ($1.16 \times 10^5$) |
| Example 21 | Compound 21 | (structure) | 505 ($1.10 \times 10^5$) | 505 ($1.10 \times 10^5$) |
| Example 22 | Compound 22 | (structure) | 500 ($1.05 \times 10^5$) | 500 ($1.05 \times 10^5$) |
| Example 23 | Compound 23 | (structure) | 503 ($1.10 \times 10^5$) | 503 ($1.10 \times 10^5$) |
| Example 24 | Compound 24 | (structure) | 515 ($1.25 \times 10^5$) | 515 ($1.25 \times 10^5$) |

TABLE 8-continued

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 25 | Compound 25 | | 477 ($1.08 \times 10^5$) | 477 ($1.08 \times 10^5$) |
| Example 26 | Compound 26 | | 490 ($1.10 \times 10^5$) | 490 ($1.10 \times 10^5$) |
| Comparative Example 2 | Cuprizone | | 330 ($7.0 \times 10^3$) | 330 ($9.0 \times 10^3$) |

TABLE 9

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 27 | Compound 27 | | 470 ($8.50 \times 10^4$) | 470 ($8.50 \times 10^4$) |
| Example 28 | Compound 28 | | 475 ($9.20 \times 10^4$) | 475 ($9.20 \times 10^4$) |
| Example 29 | Compound 29 | | 472 ($9.50 \times 10^4$) | 472 ($9.50 \times 10^4$) |
| Example 30 | Compound 30 | | 455 ($5.30 \times 10^4$) | 455 ($8.80 \times 10^4$) |

TABLE 9-continued

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 31 | Compound 31 | 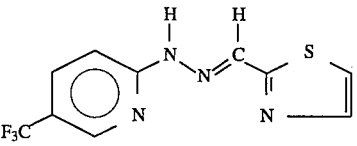 | 460 (6.60 × 10⁴) | 460 (9.40 × 10⁴) |
| Example 32 | Compound 32 | 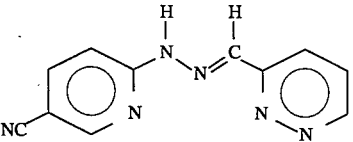 | 470 (5.20 × 10⁴) | 470 (8.60 × 10⁴) |
| Example 33 | Compound 33 | 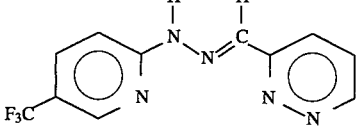 | 475 (6.50 × 10⁴) | 475 (9.30 × 10⁴) |
| Example 34 | Compound 34 | 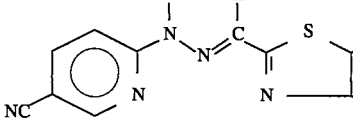 | 498 (5.80 × 10⁴) | 498 (9.70 × 10⁴) |
| Example 35 | Compound 35 | 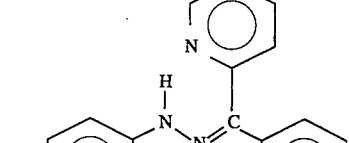 | 473 (8.70 × 10⁴) | 473 (8.70 × 10⁴) |
| Comparative Example 2 | Cuprizone | | 330 (7.0 × 10³) | 330 (9.0 × 10³) |

TABLE 10

| | Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|---|
| Example 36 | Compound 36 | 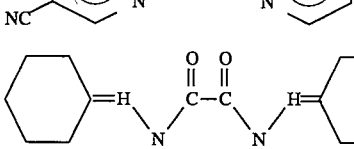 | 484 (9.85 × 10⁴) | 484 (9.85 × 10⁴) |

TABLE 10-continued

| Compound | Structure of Compound | PH7 Maximum absorption wavelength (nm) (molar absorptivity) (l/mol/cm) | PH9 Maximum absorption wavelength (nm) (molar absorptivity) (l/mol/cm) |
|---|---|---|---|
| Example 37 Compound 37 | | 490 (1.00 × 10⁵) | 490 (1.00 × 10⁵) |
| Example 38 Compound 38 | | 488 (1.00 × 10⁵) | 488 (1.00 × 10⁵) |
| Comparative Example 2 Cuprizone | | 330 (7.0 × 10³) | 330 (9.0 × 10³) |

As described in the foregoing, it is demonstrated that the hydrazone compounds of the present invention can be easily synthesized, that they have excellent nonlinearity to generate harmonics efficiently. Hence, the hydrazone compounds of the present invention are applicable to the field of optical electronics in which a nonlinearity phenomenon is utilized, such as harmonics generation, a high-speed optical shutter, an optical bistable device. Furthermore, the hydrazone compounds of the present invention can form organic metal complexes having a large molar absorptivity by coordinating to specific metal ions. Making use of the metal complex formation reaction, the hydrazone compounds of the present invention can be used as highly-sensitive coloring chelation agents in quantitative analysis of trace metal ions by means of absorption spectrophotometry.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A hydrazone compound represented by the following formula (1):

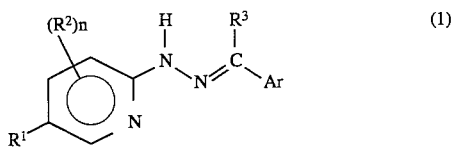

wherein

Ar is a nitrogen-containing aromatic heterocyclic group selected from the group consisting of 2-pyridyl, 2-imidazolyl, 4-imidazolyl, 3-pyrazolyl, 2-thiazolyl, 3-pyridazinyl, 2-pyrimidinyl, 4-pyrimidinyl, 1-phthalazinyl, 2-quinazolinyl, 2-benzothiazolyl, 2-benzimidazolyl, 2-quinolyl, 1-isoquinolyl, and 3-isoquinolyl, and said Ar binds to the hydrazone carbon at the α position with respect to a nuclear nitrogen atom; all of these groups being unsubstituted or substitute by methyl;

$R^1$ is selected from the group consisting of nitro, cyano and trifluoromethyl;

$R^2$ is selected from the group consisting of nitro, cyano, trifluoromethyl, halogen and substituted or non-substituted alkyl;

$R^3$ is selected from the group consisting of alkyl, aryl, 2-pyridyl, 2-imidazolyl, 4-imidazolyl, 3-pyrazolyl, 2-thiazolyl, 2-pyrrolyl, 3-indolyl, 2-furyl, 2-thienyl, 3-pyridyl, 4-pyridyl, 3-pyridazinyl, 2-pyrimidinyl, 4-pyrimidinyl, 2-pyrazinyl, 3-cinnolinyl, 1-phthalazinyl, 2-quinazolinyl, 4-quinaolinyl, 2-quinoxalinyl, 2-benzothiazolyl, 2-benzimidazolyl, 2-quinolyl, 1-isoquinolyl, 3-isoquinolyl, 6-phenanthridinyl and hydrogen; all these groups except hydrogen being either substituted or not substituted; and n is zero or an integer ranging from 1 to 3, with the provisos that when Ar is a 2-pyridyl, $R^1$ is nitro, and $R^3$ is hydrogen, n cannot be zero and that when Ar is 2- or 4-imidazolyl, $R^2$ is trifluoromethyl or halogen, and $R^3$ is hydrogen, $R^1$ can not be trifluoromethyl.

2. The hydrazone compound according to claim 1, wherein said Ar is a nitrogen-containing aromatic heterocyclic group selected from the group consisting of a 2-pyridyl, 3-pyridazinyl, 2-pyrimidinyl, 4-pyrimidinyl, 2-quinolyl, 1-isoquinolyl, 3-isoquinolyl, 1-phthalazinyl, 2-quinazolinyl, 2-benzimidazolyl, and 2-benzothiazolyl and said Ar binds to a hydrazone carbon at the α position with respect to a nuclear nitrogen atom.

3. The hydrazone compound according to claim 1, wherein said $R^1$ is cyano or trifluoromethyl.

4. The hydrazone compound according to claim 1, represented by the following formula (2):

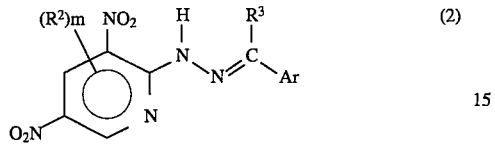

(2)

wherein Ar, $R^2$ and n are as defined in claim 2; and m is an integer from 0 to 2.

5. The hydrazone compound according to claim 1 represented by the following formula (3):

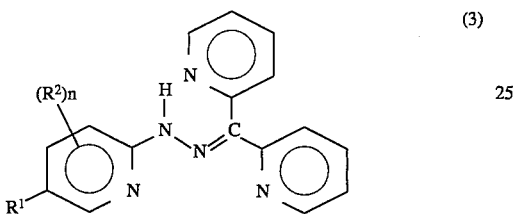

(3)

wherein $R^1$, $R^2$ are n are as defined in claim 1.

6. A hydrazone compound represented by the following Formula (1) having a melting point not lower than 189° C.:

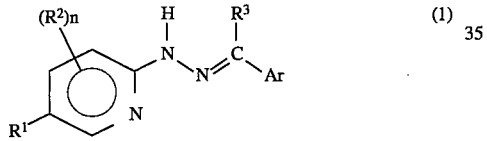

(1)

wherein

Ar is selected from the group consisting of 2-pyridyl, 2-imidazolyl, 4-imidazoly, 3-pyrazolyl, 2-thiazolyl, 2-pyrrolyl, 3-indolyl, 2-thienyl, 4-pyridyl, 3-pyridazinyl, 2-pyrimidinyl, 4-pyrimidinyl, 2-pyrazinyl, 3-cinnolinyl, 1-phthalazinyl, 2-quinazolinyl, 4-quinazolinyl, 2-quinoxalinyl, 2-benzothiazolyl, 2-benzimidazolyl, 2-quinolyl, 1-isoquinolyl, 3-isoquinolyl, and 6-phenanthridinyl; all these groups being either substituted or non-substituted;

$R^1$ is selected from the group consisting of nitro, cyano and trifluoromethyl;

$R^2$ is selected from the group consisting of nitro, cyano, trifluoromethyl, halogen and substituted or non-substituted alkyl;

$R^3$ is selected from the group consisting of alkyl, aryl, 2-pyridyl, 2-imidazolyl, 4-imidazolyl, 3-pyrazolyl, 2-thiazolyl, 2-pyrrolyl, 3-indolyl, 2-furyl, 2-thienyl, 3-pyridyl, 4-pyridyl, 3-pyridazinyl, 2-pyrimidinyl, 4-pyrimidinyl, 2-pyrazinyl, 3-cinnolinyl, 1-phthalazinyl, 2-quinazolinyl, 4-quifiazolinyl, 2-quinoxalinyl, 2-benzothiazolyl, 2-benzimidazolyl, 2-quinolyl, 1-isoquinolyl, 3-isoquinolyl, 6-phenanthridinyl and hydrogen; all these groups except hydrogen being either substituted or not substituted; and n is zero or an integer from 1 to 3, with the provisos that when Ar is 2-pyridyl, $R^1$ is nitro, and $R^3$ is hydrogen, n can not be zero and that when Ar is 2- or 4-imidazolyl, 2-thienyl or 2-pyrrolyl, $R^2$ is trifluoromethyl or halogen and $R^3$ is hydrogen, $R^1$ can not be trifluoromethyl.

* * * * *